United States Patent [19]
Miura et al.

[11] Patent Number: 5,399,785
[45] Date of Patent: Mar. 21, 1995

[54] TYROSINASE ACTIVITY INHIBITOR

[75] Inventors: Yasutaka Miura, Takatsuki; Yasuhiro Kinoshita; Yoshikazu Yamamoto, both of Neyagawa; Kunio Takahashi, Urawa; Kiyotaka Koyama; Kaoru Takatori, both of Higashikurume, all of Japan

[73] Assignee: Nippon Paint Co., Ltd., Osaka, Japan

[21] Appl. No.: 102,067

[22] Filed: Aug. 4, 1993

[30] Foreign Application Priority Data

Aug. 5, 1992 [JP] Japan .................................. 4-208808

[51] Int. Cl.⁶ ...................... C07C 39/10; C07C 39/08
[52] U.S. Cl. ................................. 568/766; 568/722; 568/763; 568/772
[58] Field of Search ................ 568/763, 766, 772, 722

[56] References Cited

U.S. PATENT DOCUMENTS

| | | | |
|---|---|---|---|
| 3,865,884 | 2/1975 | Agusto et al. | 568/772 |
| 4,160,113 | 7/1979 | Müller et al. | 568/772 |
| 4,172,960 | 10/1979 | Baldwin et al. | 568/772 |

OTHER PUBLICATIONS

Arlt et al. "Chemical Abstracts" vol. 73(5) 25,114R (Aug. 1970).
Chavin "Chemical Abstracts" vol. 76(7) 30,865X (Jan 1972).
Shriwiressin et al. "Chemical Abstracts" vol. 76() 95,161t (1976).
Habu et al. "Chemical Abstracts" vol. 83(2) 18,937j (Jul. 1973).
Panteleimonova et al. "Chemical Abstracts" vol. 93(23) 216,002u (Dec. 1980).
Hayashi et al. "Chemical Abstracts" vol. 100(11) 82,997a (May 1984).
Picardo et al. "Chemical Abstracts", vol. 106(21) 168,626t (May 1987).
Passi et al. "Chemical Abstracts" No. 1 107() 70269w (Aug. 1987).
Barrett et al. "Chemical Abstracts" vol. 107(9) 74,670t (Aug. 1987).
Uetani et al. "Chemical Abstracts" vol. 112(26) 243,094 (Jun. 1990).
Russell et al. "J. Amer. Chem. Soc" vol. 61 pp. 1441-1443 (Jun. 1940).

*Primary Examiner*—Werren B. Lone
*Attorney, Agent, or Firm*—Townsend & Banta

[57] ABSTRACT

Disclosed is a chemically stable tyrosinase activity inhibitor having high tyrosinase activity inhibition effect and low toxicity. The tyrosinase activity inhibitor has a structure of the formula:

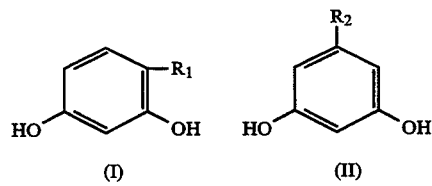

or

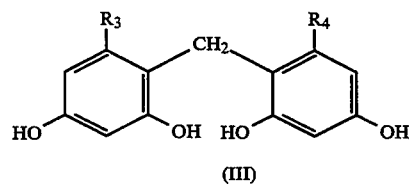

wherein $R_1$, $R_3$ and $R_4$ are a hydrogen atom or an alkyl or alkenyl group having 1 to 9 carbon atoms, and $R_2$ is an alkyl or alkenyl group having 2 to 9 carbon atoms.

8 Claims, 2 Drawing Sheets

TYROSINASE ACTIVITY INHIBITOR

FIELD OF THE INVENTION

The present invention relates to a tyrosinase activity inhibitor which is useful for facial cosmetics, stain-resistant substances for marine paint and melanin production inhibitors.

BACKGROUND OF THE INVENTION

Several phenolic compounds have hitherto been known as tyrosinase activity inhibitors, and some of them are used for the application such as facial cosmetics and the like. However, these phenolic compounds often have a problem on safety for human body, chemical stability and efficacy.

As the tyrosinase activity inhibitor, hydroquinones and resorcinols having a long chain alkyl group at 4-position are known at present. However, the tyrosinase activity inhibitions as described in Japanese Patent Kokai Nos. 61-21007, 61-21008, 61-21009, 61-21010, 61-21011 and 61-21012 functions as non-competitive antagonist and seems toxic to human body in view of maintenance of hemostasis in human body. Since the tyrosinase activity inhibitor as described in Japanese Patent Kokai No. 3-28462 has a long chain alkyl group at 4-position of resorcinol, it is inferior in solubility to water. Therefore, it is difficult to use for normal cosmetics, satisfactorily. Further, arbutin which has hitherto been used has toxicity, and tranexamic acid described in Japanese Patent Kokai No. 4-169515 has low tyrosinase activity inhibition effect.

OBJECTS OF THE INVENTION

Main object of the present invention is to provide a chemically stable tyrosinase activity inhibitor having high tyrosinase activity inhibition effect and low toxicity.

This object as well as other objects and advantages of the present invention will become apparent to those skilled in the art from the following description.

SUMMARY OF THE INVENTION

According to the present invention, there is provided a tyrosinase activity inhibitor having a structure of the formula:

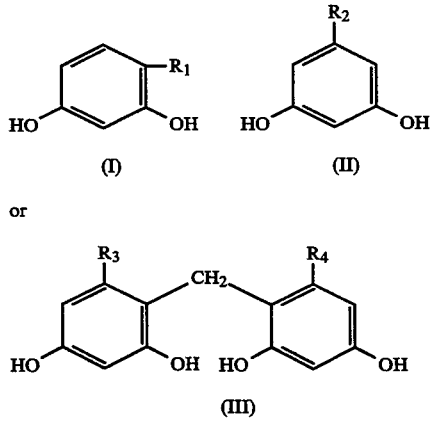

wherein $R_1$, $R_3$ and $R_4$ are a hydrogen atom or an alkyl or alkenyl group having 1 to 9 carbon atoms, and $R_2$ is an alkyl or alkenyl group having 2 to 9 carbon atoms.

DETAILED DESCRIPTION OF THE INVENTION

Preferably, the tyrosinase activity inhibitor of the present invention is at least one sort which is selected from the group consisting of the compounds of the formula (III). More preferably, it is tyrosinase activity inhibitor having a structure of the formula:

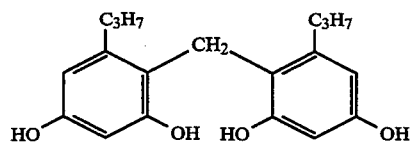

A method for preparing the compounds having a structure of the formulas (I), (II) and (III) is not specifically limited. These compounds may be synthesized by a method known to the art. For example, they can be synthesized by the following methods, respectively.

Process for the production of the compound of the formula (I)

Firstly, an alkylcarboxylic acid is reacted with resorcinol to obtain a 2,4-dihydroxyalkylphenone. This is then reduced with zinc amalgam obtained from zinc and mercuric chloride to give a 4-alkylresorcinol.

Process for the production of the compound of the formula (II)

Firstly, 1,3-dimethoxy-5-benzoyl chloride is reacted with an alkylmagnesium bromide to obtain a 1,3-dimethoxy-alkylphenone. This is then reduced with zinc amalgam obtained from zinc and mercuric chloride. The reaction is promoted by adding concentrated hydrochloric acid (10 to 50 cc) every one hour. After the completion of the reaction, the reaction product is cooled and purified by a known method to obtain a 5-alkylresorcinol.

Process for the production of the compound of the formula (III)

Firstly, a 1,3-dimethoxy-5-alkylbenzene is reacted with phenoxyacetyl chloride and aluminum chloride to obtain a 6,6'-dialkyl-2,2',4,4'-tetramethoxydiphenylmethane. This is then hydrolyzed by a known method to obtain a 6,6'-dialkyl-2,2',4,4'-tetrahydroxydiphenylmethane.

When the tyrosinase activity inhibitor of the present invention is used for cosmetics, at least one sort of a compound selected from the compounds of the formulas (I), (II) and (III) is dissolved or dispersed in bases (e.g. oils such as olive oil, mink oil, etc.; waxes such as lanolin, beeswax, etc.; hydrocarbons such as vaseline, squalane, etc.; esters such as isopropyl palmitate, etc.; higher alcohols such as cetyl alcohol, lauryl alcohol, etc.; higher fatty acids such as stearic acid, palmitic acid, etc.; sterols such as cholesterol, etc.) and alcohols (e.g. ethanol, isopropyl alcohol, propylene glycol, etc.), which are normally used for cosmetics. Thus, the tyosinase activity inhibitor of the present invention can be widely applied for various cosmetics (e.g. various basic cosmetics such as cosmetic cream, milky lotion, skin lotion, pack, cleansing cream, etc.; various makeup cosmetics such as foundation, cheek rouge, blusher, lipstick, etc.; other cosmetics such as soap, shampoo, rinse, perfume, cologne, etc.). The trypsine activity inhibitor can be used in combination with various additives for cosmetics (e.g. surfactants, solvents, pigments, perfumes, preservatives, antioxidants, humectants, vitamin E, organic and plant extracts, other additives, etc.). Further, above-mentioned various cosmetics can take any form such as solution, emulsion, ointment, oil, wax, gel, sol, powder, spray and the like.

The amount of the tyrosinase activity inhibitor to be formulated varies depending upon the form of the cosmetic used. In principle, it may be present in an active amount. Normally, the tyrosinase activity inhibitor is formulated in the amount of 0.001 to 20% by weight, preferably 0.01 to 5% by weight, based on the total weight of the cosmetic composition.

The tyrosinase activity inhibitor of the present invention has low toxicity and irritation to skin as well as high stability to light and heat. Further, it has high stability to various cosmetic bases and additives, and can be used in combination with cosmetic bases and additives.

As described above, according to the present invention, there is provided a chemically stable tyrosinase activity inhibitor having high tyrosinase activity inhibition effect and low toxicity.

EXAMPLES

Figure 1:
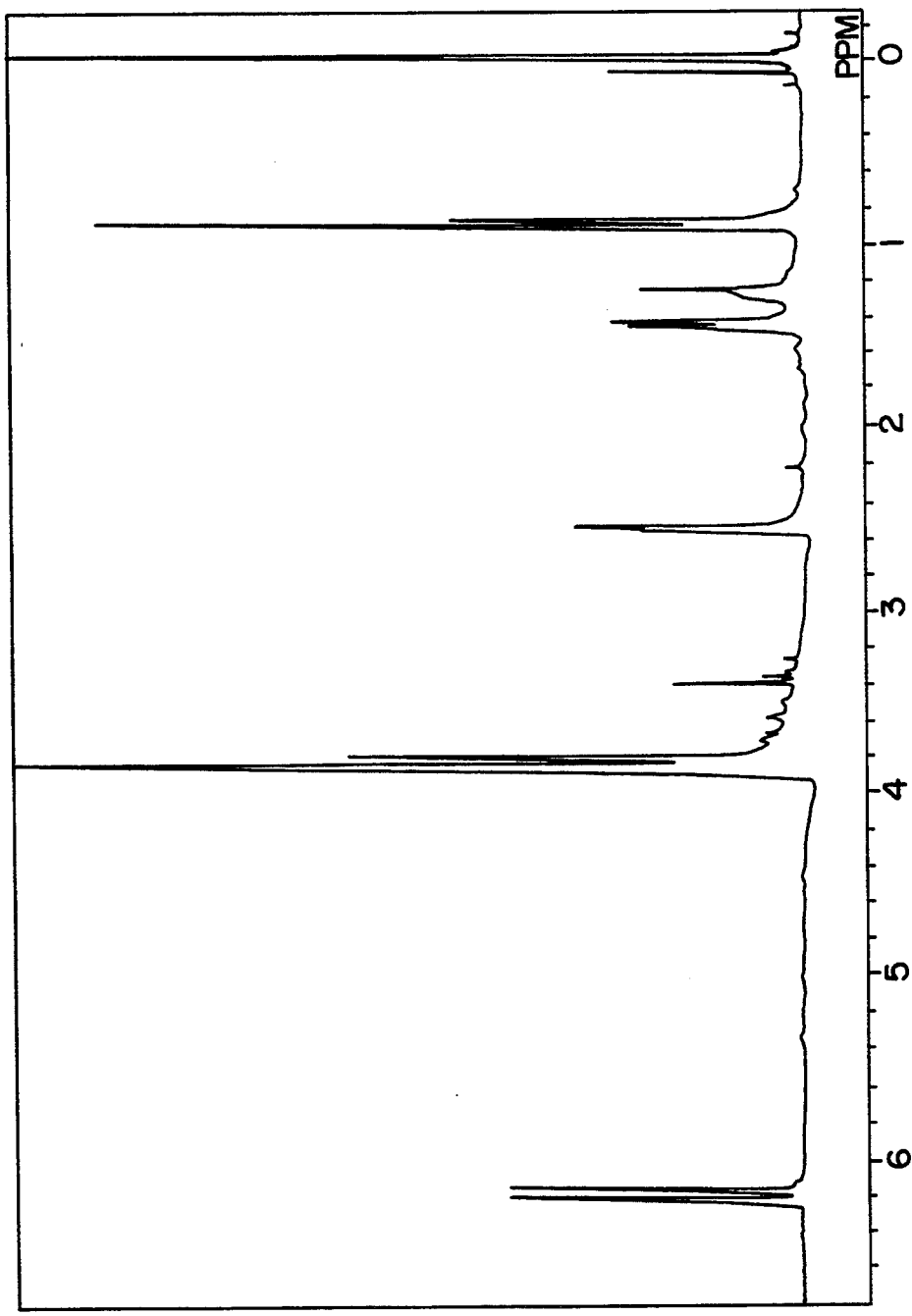
FIG. 1 shows a $^1$H-NMR chart of the compound obtained in Example 3.

The following Examples further illustrate the present invention in detail but are not to be construed to limit the scope thereof.

Synthesis 1

Synthesis of 4-ethylresorcinol

Zinc chloride (151 g) was dissolved in butyric acid (162 g). Then, resorcinol (110 g) was added and the mixture was reacted at 150° C. for 20 minutes. After the completion of the reaction, concentrated hydrochloric acid (250 ml) and water (250 ml) were added to the reaction product, which was cooled and purified by a normal method to obtain 100 g of a compound, 2,4-dihydroxyethylphenone. Then, the reduction was conducted by adding water (300 cc), concentrated hydrochloric acid (300 cc) and 2,4-dihydroxyethylphenone (100 g) to zinc amalgam obtained from zinc (400 g) and mercuric chloride (20 g). Further, concentrated hydrochloric acid (10 to 15 cc) was added every one hour. After the completion of the reaction, the reaction solution was cooled and saturated with sodium chloride, and then extracted with ether to obtain 88 g of 4-ethylresorcinol.

Synthesis 2

Synthesis of 5-methylresorcinol

Methylmagnesium bromide (35 g) was added to 1,3-dimethoxy-5-benzoyl chloride (100 g) to obtain 1,3-dimethoxy-methylphenone in a yield of 45%. Then, the reduction was conducted by adding water (300 cc), concentrated hydrochloric acid (300 cc) and 1,3-dimethoxy-methylphenone (100 g) to zinc amalgam obtained from zinc (400 g) and mercuric chloride (20 g). Further, concentrated hydrochloric acid (10 to 15 cc) was added every one hour. After the completion of the reaction, the reaction solution was cooled and saturated with sodium chloride, and then extracted with ether to obtain 40 g of 1,3-dimethoxy-5-methylbenzene. Hydrogen iodide was added to the resulting 1,3-dimethoxy-5-methylbenzene and stirred at 115° to 125° C. for 3 hours under nitrogen atmosphere. After cooling, the product was extracted with methylene chloride to obtain 30 g of 5-methylresorcinol.

Synthesis 3

Synthesis of 6,6'-di-n-propyl-2,2',4,4'-tetrahydroxydiphenylmethane

Figure 2:
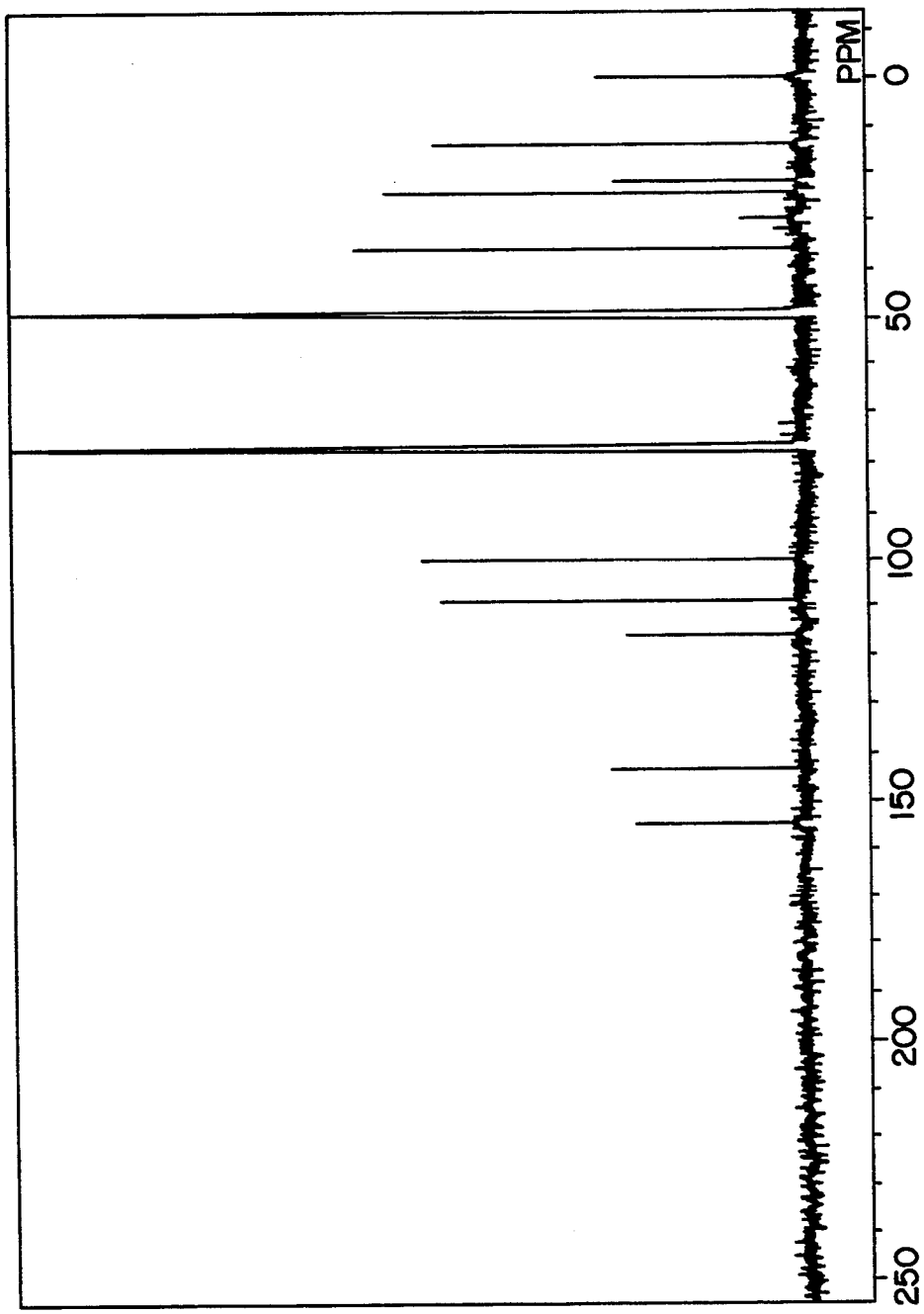
FIG. 2 shows a $^{13}$C-NMR chart of the compound obtained in Example 3

To benzene (70 ml) were added 1,3-dimethoxy-5-propylbenzene (11 g), phenoxyacetyl chloride (11 g) and aluminum chloride (9 g), followed by stirring at 5° C. for 1.5 hours. The mixture was hydrolyzed with hydrochloric acid under ice cooling and extracted with ether to obtain 0.3 g of 6,6'-di-n-propyl-2,2',4,4'-tetramethoxydiphenylmethane. Hydrogen iodide was added to the resulting 6,6'-di-n-propyl-2,2',4,4'-tetramethoxydiphenylmethane and stirred at 115° to 125° C. for 3 hours. After cooling, the mixture was extracted with methylene chloride to obtain 0.3 g of 6,6'-di-n-propyl-2,2',4,4'-tetrahydroxydiphenylmethane. The resulting compound was subjected to $^1$H-NMR and $^{13}$C-NMR spectrum and the charts thereof are shown in FIGS. 1 and 2.

EXAMPLE

Measurement of tyrosinase activity inhibition % of tyrosinase activity inhibitors obtained in Synthesis 1 to 3 and other inhibitors, as shown in Table 2, which is within or outside (contrast) the present claims, and which were prepared as generally described in Synthesis 1 to 3

The measurement was conducted by the following method.

(1) Reaction reagent

The reaction reagent used are as follows:
Substrate: 2 mM L-DOPA (Wako Junyaku Co.)
Buffer: 0.1 mM phosphate-potassium solution (pH 6.8)
Inhibitor: 1% solution of the compound of the formula (I), 4-ethylresorcinol, compound of the formula (II), 5-methylresorcinol and compound of the formula (III), 6,6'-di-n-propyl-2,2',4,4'-tetrahydroxydiphenylmethane
Enzyme: tyrosinase (Sigma Co.), 0.5 mg/ml (2) Measurement of tyrosinase activity inhibition %

Preparation of reaction solution

In the case of measuring tyrosinase activity inhibition %, a sample solution (No.1 to No.3) was prepared in a spectrophotometric cell (1 ml), by mixing each ingredient in the following formulation shown in Table 1.

TABLE 1

| | Formulation of sample solution (ml) | | |
|---|---|---|---|
| | No. 1 | No. 2 | No. 3 |
| Buffer | 0.50 | 0.50 | 0.50 |
| Substrate | — | 0.20 | 0.20 |
| Inhibitor | — | — | 0.10 |
| Deionized water | 0.48 | 0.28 | 0.18 |

Measurement

An enzyme solution (0.20 ml) was added to the cell. Three minutes later, the measurement of temporal changes of an absorbance (417 nm) by means of a spectrophotometer had started. The inhibition % was calculated based on the following equation:

$$\text{Inhibition \%} = [1-(Ab.3-Ab.1/Ab.2-Ab.1)] \times 100$$

wherein Ab.2 is an absorbance of No.2 solution, Ab.1 is an absorbance of No.1 solution (at the time when the absorbance of No.2 solution exhibits maximum) and Ab.3 is an absorbance of No.3 solution (at the time when the absorbance of No.2 solution exhibits maximum). $IC_{50}$, which shows a concentration ($\mu$M) of tyrosinase activity inhibitor when the tyrosinase activity inhibition (%) is 50%, are shown in Table 2.

TABLE 2

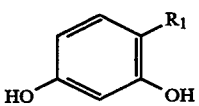

| Variation of R | $R_1$ | $R_2$ |
|---|---|---|
| Methyl | 8 | 5,000 (contrast) |
| Ethyl | 2 | 700 |
| n-Propyl | 0.9 | 500 |
| n-Pentyl | 0.8 | 200 |
| n-Heptyl | 0.7 | 200 |
| n-Nonyl | 0.9 | 200 |
| Compound of Example 3 | 25 | |

Numbers in Table 2 have a unit of $\mu$M.

What is claimed is:

1. A method for inhibiting tyrosinase activity in which a compound represented as follows is used:

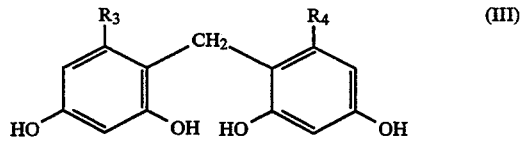

wherein $R_3$ and $R_4$ are a hydrogen atom or an alkyl or alkenyl group having 1 to 9 carbon atoms.

2. The method for inhibiting tyrosinase activity according to claim 1, wherein $R_3$ and $R_4$ are a propyl group.

3. The method for inhibiting tyrosinase activity according to claim 1, wherein the compound is: 6,6'-Di-n-propyl-2,2', 4,4'-tetrahydroxy-diphenylmethane.

4. A method of inhibiting tyrosinase activity comprising applying to the skin a cosmetic composition comprising a compound having the formula:

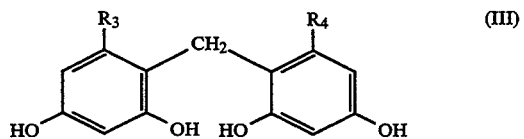

wherein $R_3$ and $R_4$ are hydrogen or alkyl or alkenyl having 1 to 9 carbon atoms.

5. The method of claim 4, wherein $R_3$ and $R_4$ are propyl.

6. The method of claim 4, wherein the compound of formula III comprises 0.001 to 20% by weight, based on the total weight of the cosmetic composition.

7. The method of claim 4, wherein the compound of formula III comprises 0.01 to 5% by weight, based on the total weight of the cosmetic composition.

8. The method of claim 4, wherein the cosmetic is a facial cosmetic.

* * * * *